(12) United States Patent
Tadion

(10) Patent No.: US 6,280,690 B1
(45) Date of Patent: Aug. 28, 2001

(54) METHODS AND APPARATUS FOR OBTAINING TRANSMISSION SPECTRA OF LIQUID AND SOLID SAMPLES

(76) Inventor: Jay Tadion, 75 Avenue General Guisan, 1009-Pully/Lausanne (CH)

(*) Notice: Subject to any disclaimer, the term of this patent is extended or adjusted under 35 U.S.C. 154(b) by 0 days.

(21) Appl. No.: 09/222,757

(22) Filed: Dec. 30, 1998

(30) Foreign Application Priority Data

Dec. 30, 1997 (GB) .................................................. 9727390

(51) Int. Cl.⁷ .................................................. G01N 21/00
(52) U.S. Cl. ........................ 422/102; 422/104; 436/164; 356/244
(58) Field of Search ............................. 422/99, 100, 102, 422/104; 436/164; 245/7–8; 250/339.07; 356/244

(56) References Cited

U.S. PATENT DOCUMENTS

| | | | | |
|---|---|---|---|---|
| 966,599 | * | 8/1910 | Reynolds | .................................. 245/8 |
| 2,694,852 | * | 11/1954 | Rogers | ..................................... 245/8 |
| 3,049,796 | * | 8/1962 | Pall | ........................................... 245/8 |
| 5,453,252 | | 9/1995 | Truett | .................................... 436/164 |
| 5,519,218 | * | 5/1996 | Chang | ............................. 250/339.07 |
| 5,764,355 | * | 6/1998 | Gagnon et al. | ....................... 356/244 |
| 5,786,226 | | 7/1998 | Böcker et al. | ....................... 436/164 |

OTHER PUBLICATIONS

R. M. Ressler et al. Applied Optics 1967, 6, 893–896, May 1967.*

* cited by examiner

Primary Examiner—Arlen Soderquist
(74) Attorney, Agent, or Firm—Everett G. Diederiks, Jr.

(57) ABSTRACT

A sample holder for spectroscopy is formed by pressing a wire mesh so that its thickness is reduced. Preferably the mesh is formed of stainless steel strands of 25 microns thickness, and is pressed to a thickness of 10–20 microns.

15 Claims, 7 Drawing Sheets

METHODS AND APPARATUS FOR OBTAINING TRANSMISSION SPECTRA OF LIQUID AND SOLID SAMPLES

BACKGROUND OF THE INVENTION

1. Field of the Invention

This invention relates to an improved method and apparatus for obtaining the transmission spectra of liquid, paste and solid samples, and in particular to sample holders. It is applicable over a wide spectral range, but especially in the mid infrared region where absorption coefficients are often very high and corresponding sample thicknesses need to be very small, typically of the order of 10 microns for pure substances or simple mixtures.

2. Discussion of the Prior Art

There are a number of methods known for supporting samples for infrared spectroscopy. For powdered solids the sample is normally held within pressed discs of infrared transmitting material, typically KBr. The disadvantage of this method is that this has only a limited spectral range due to the absorption of KBr.

Spaced sample cells of infrared transmitting material are also used to support liquid samples. However, these typically have a limited spectral range. Other disadvantages are difficulty of construction and use, cost, lack of chemical inertness and limited spectral range.

Another known method for supporting liquid samples involves the use of thin films of porous material. Such discs can be obtained from 3M, and consist of Teflon or polythene. Teflon and polythene have absorption bands, but in different regions of the spectrum. Therefore it is possible to cover a wide spectral range by the selective use of the two materials. However, it is inconvenient to use different materials for different spectral regions and the absorption bands again reduce the quality of the recorded spectra.

Another method for supporting liquid samples is the use of coarse gauzes which take up liquid by capillary action. Janos Technology Inc produce screens formed by such a gauze (ECRAN (RTM) Screen Cells), which are described in U.S. Pat. No. 5,453,252. The gauze is formed from polymer coated glass fibres, onto which a liquid or powdered solid is placed. The gauze is approximately 300 microns thick where the fibres cross each other, and the holes between the fibres are approximately 1 mm across. Solid samples can also by supported by such screens.

The disadvantage of the above screens is their thickness and hole size. For many samples a thickness of 10–20 microns is preferable, especially in the mid infrared region, and the thickness of 300 microns provided by the Ecran Screen Cells prevents samples being thin enough. There is also the problem that with hole sizes in the region of 1 mm, the surface tension of many liquids is not sufficient to hold the liquid in place across the holes. Solid samples may be introduced by covering the mesh with a solution of the sample in a suitable solvent and allowing the solvent to evaporate. The large hole size of the Ecran screen cell makes it extremely difficult to achieve a continuous film by this means.

SUMMARY OF THE INVENTION

The present invention seeks to overcome or at least mitigate these problems, and from a first aspect provides a spectroscopy sample holder for receiving a sample comprising a wire mesh which has been pressed to reduce its thickness.

From a second aspect the invention provides a method of forming a sample holder for spectroscopy, comprising: providing a mesh, and pressing said mesh between hardened dies so as to reduce its thickness.

By pressing a mesh, a thickness closer to that needed for optimum operation can be achieved, leading to improved results. The mesh can be pressed to a thickness considerably below mesh thicknesses available on the market. Such a mesh can support liquid, paste or solid samples.

The wires of the mesh are preferably formed from stainless steel. It is believed that the invention will improve the performance of existing meshes which, after pressing, will have a smaller thickness. Preferably, however, a mesh whose strands have a small diameter initially is used. The finest stainless steel mesh with high transmission, which it is practical to manufacture, uses wires with a diameter in the region of 25 microns. This means that a mesh formed from this wire will have a thickness of approximately 50 microns, which is well above the desired thickness of 10–20 microns. This mesh is advantageously reduced in thickness by pressing between hardened dies to reduce the overall thickness to the region of 10 to 20 microns.

When the mesh is pressed as described above, the transmission is reduced as the wires are deformed. Therefore the nominal transmission of a mesh as described is preferably in the region of 80% before pressing to reduce thickness and in the region of 60% after pressing, which is adequate for use in transmission spectroscopy.

The pressed mesh of the present invention can support liquid samples by capillary action. Solids can be sampled by wetting the mesh with a solution of the sample and allowing the solvent to evaporate, leaving a film of solid on the mesh. In both of these cases the mesh may with advantage be chemically or thermally treated to improve the wettability. It has been found that washing the mesh in hydrochloric acid followed by distilled water before use for supporting a liquid sample significantly increases its wettability.

If the transmission of a powdered sample is to be measured, the sample and the mesh can be pressed at the same time. This has the advantage that the thickness of the sample is reduced at the same time as that of the mesh.

Thus, according to a second aspect, the present invention provides a method of preparing a powdered sample for spectroscopic analysis, comprising the steps of placing the sample on a mesh, and pressing the sample into the mesh with sufficient force that the thickness of the mesh is reduced.

The mesh may be conveniently supported in a suitable frame of cardboard or other material with an open aperture, preferably circular, the size of the frame and aperture being appropriate to the spectrometer being used but typically a 15 mm diameter aperture in a suitable frame. The observed effective transmission is reduced slightly by diffraction effects and decreases slightly, in a smooth, continuous manner, from short to long wavelengths over the range of a typical infrared spectrometer. Compensation of this effect is readily achieved by recording a reference spectrum, or background, with a clean mesh in the radiation beam.

Since the mesh is electrically conducting it may conveniently be heated by passing an electric current through it in order to aid the formation of thin capillary films of viscous liquid or low melting point solid samples.

The mesh may be disposable.

BRIEF DESCRIPTION OF THE DRAWINGS

A sample holder embodying the invention and some illustrative examples of spectra recorded using a pressed mesh according to the present invention, and using a Janos ECRAN Screen Cell are shown in the accompanying drawings, in which.

DETAILED DESCRIPTION OF THE PREFERRED EMBODIMENTS

All of the spectra shown in FIGS. 1–6 were recorded using a Perkin-Elmer Paragon FTIR spectrometer, at 4 cm$^{-1}$ resolution. All of the spectra were recorded under the same conditions, after backgrounds were recorded with a clear path for the radiation beam. Where a mesh according to the present invention was used, it was a pressed from a mesh of 25 micron diameter wires with 80% transmission into a mesh of thickness of less than 20 microns and 60% transmission.

Figure 1:
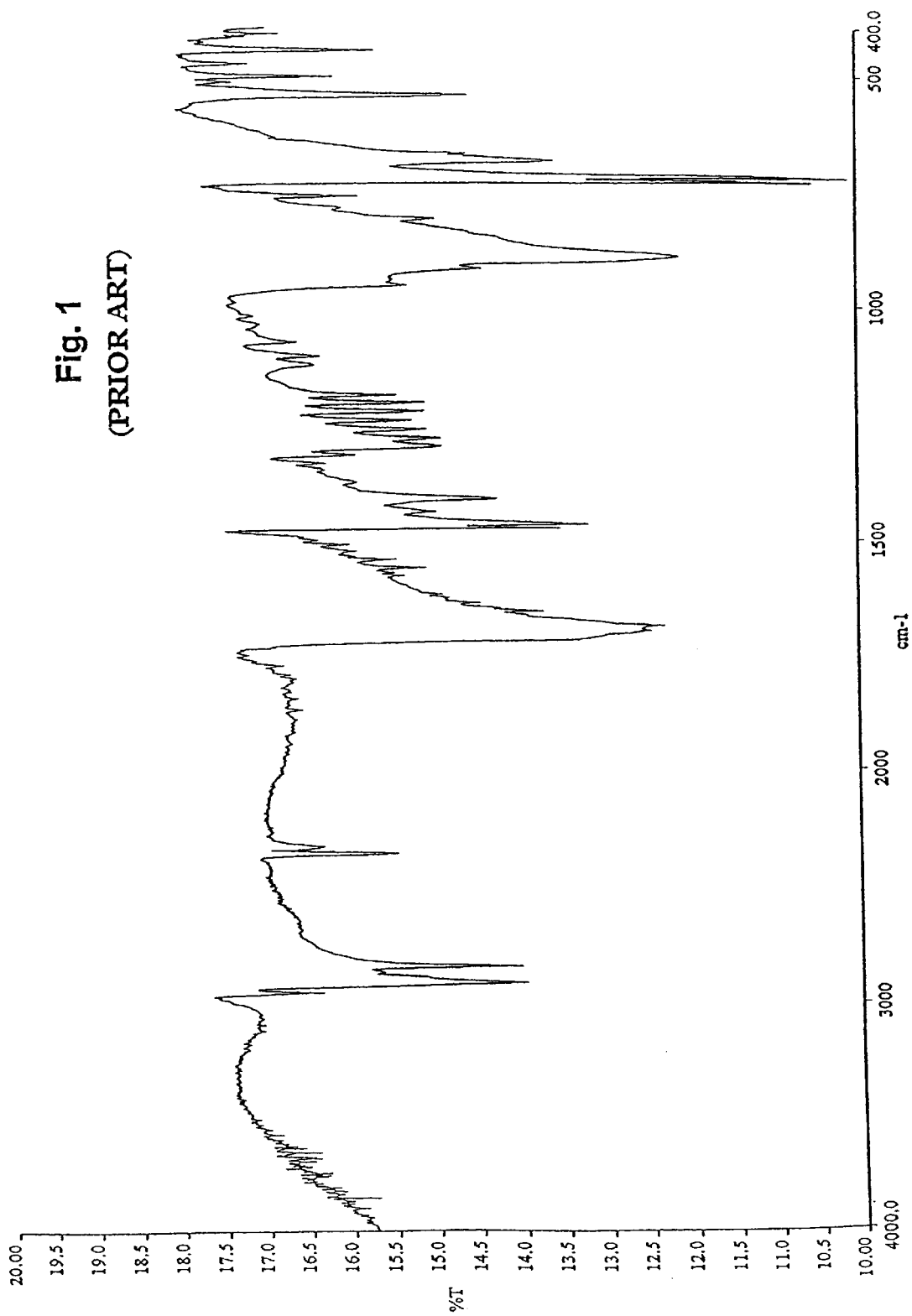
FIG. 1 shows the FTIR transmission spectrum of stearic acid mounted on a Janos ECRAN Screen Cell.
Figure 2:
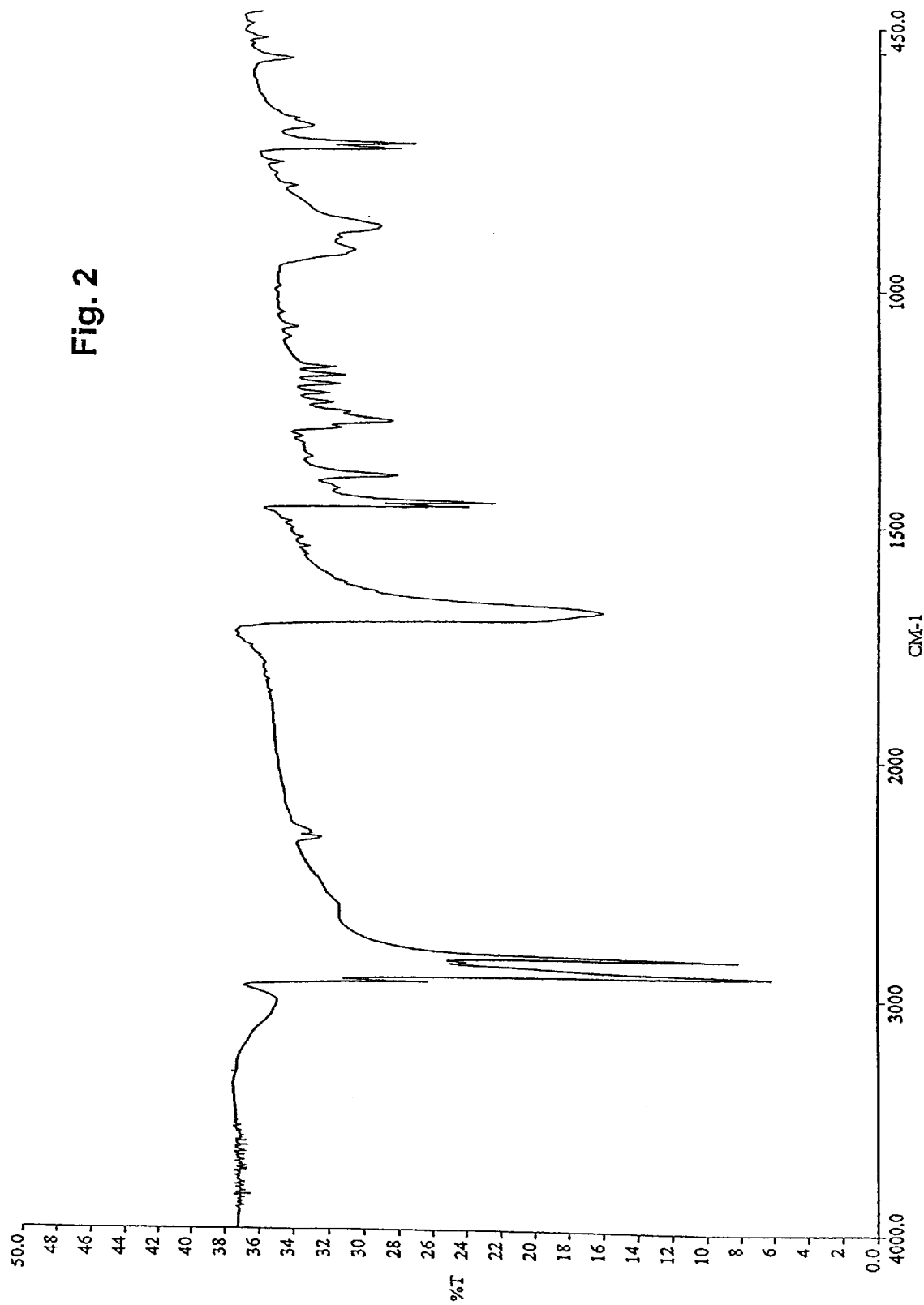
FIG. 2 shows the FTIR transmission spectrum of stearic acid mounted on a pressed mesh according to the present invention.

FIGS. 1 and 2 show the spectrum of stearic acid, as recorded when mounted on an ECRAN Screen Cell and a pressed mesh respectively. The transmission recorded using the pressed mesh was twice as high as that using the ECRAN cell. There is considerably less noise in the spectrum, and the spectral detail is much clearer.

Figure 3:
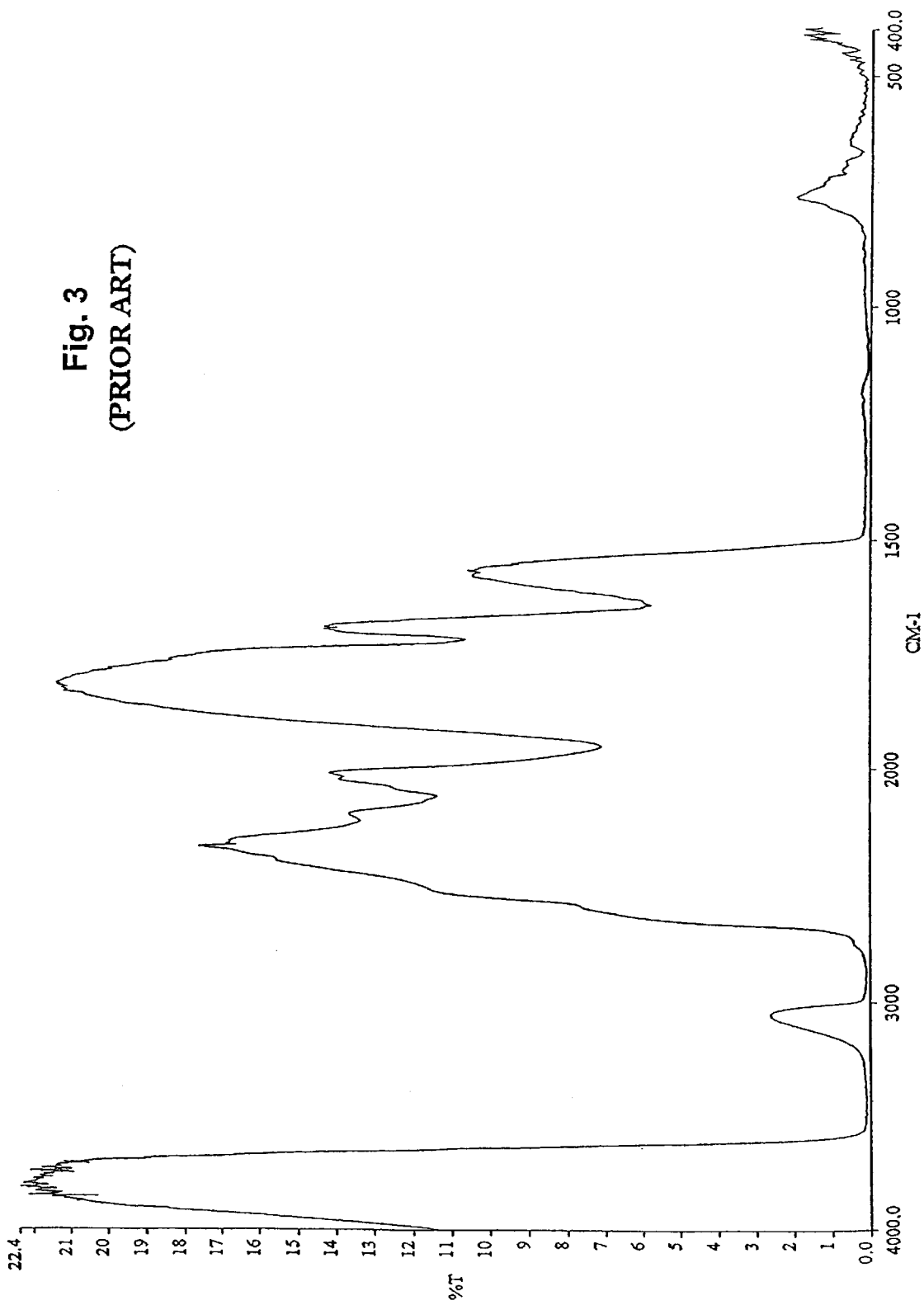
FIG. 3 shows the FTIR transmission spectrum of brake fluid mounted on a Janos ECRAN Screen Cell.
Figure 4:
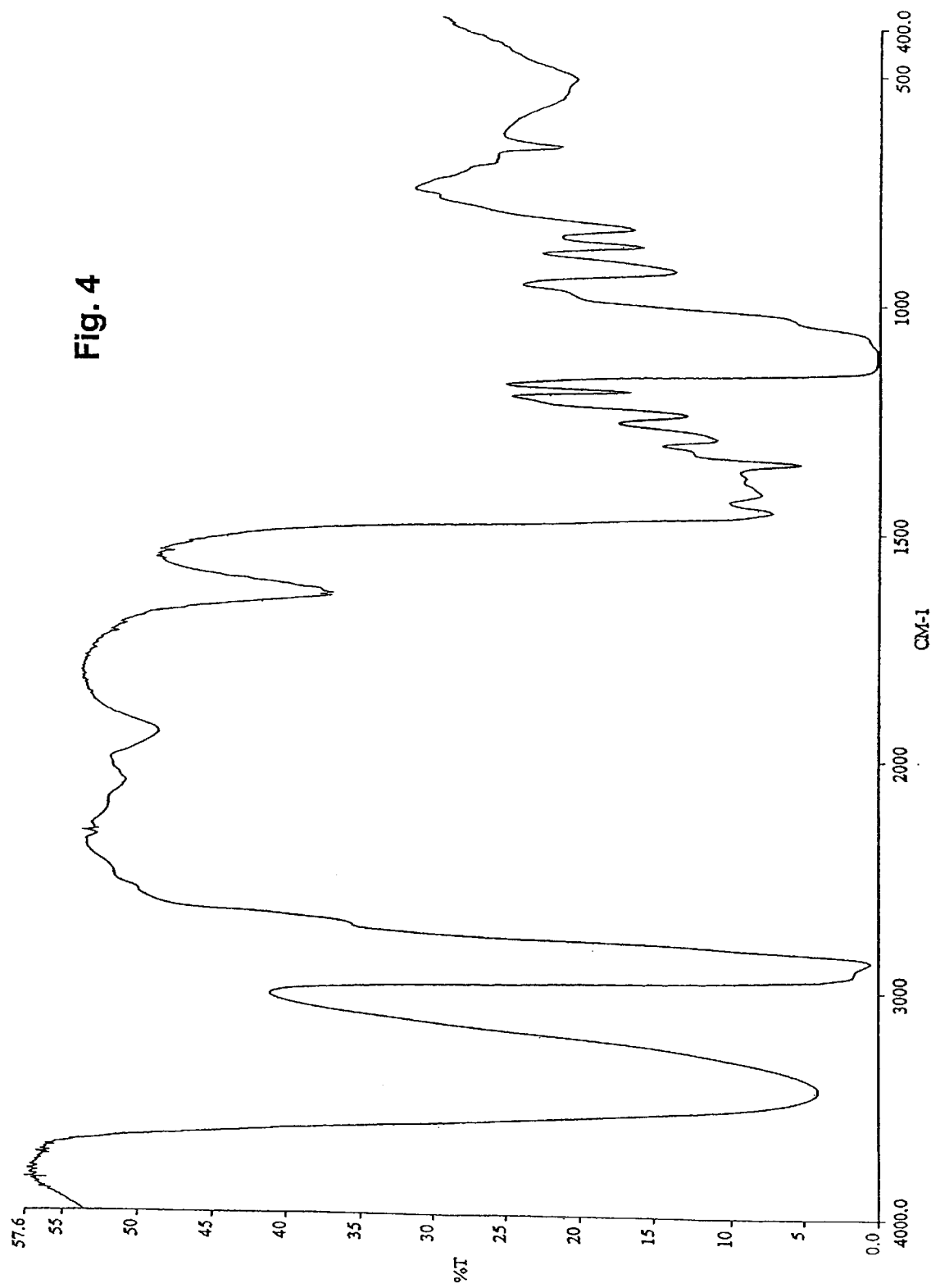
FIG. 4 shows the FTIR transmission spectrum of brake fluid mounted on a pressed mesh according to the present invention.

FIGS. 3 and 4 show the spectrum of brake fluid, as recorded when mounted on an ECRAN Screen Cell and a pressed mesh respectively. Again, the transmission is in general twice as high using the mesh of the invention: the sample thickness with the Ecran cell is so great that for radiation longer than 1500 cm$^{-1}$ no spectral detail is visible, whereas when the pressed mesh is used spectral detail is visible even at 400 cm$^{1}$.

Figure 5:
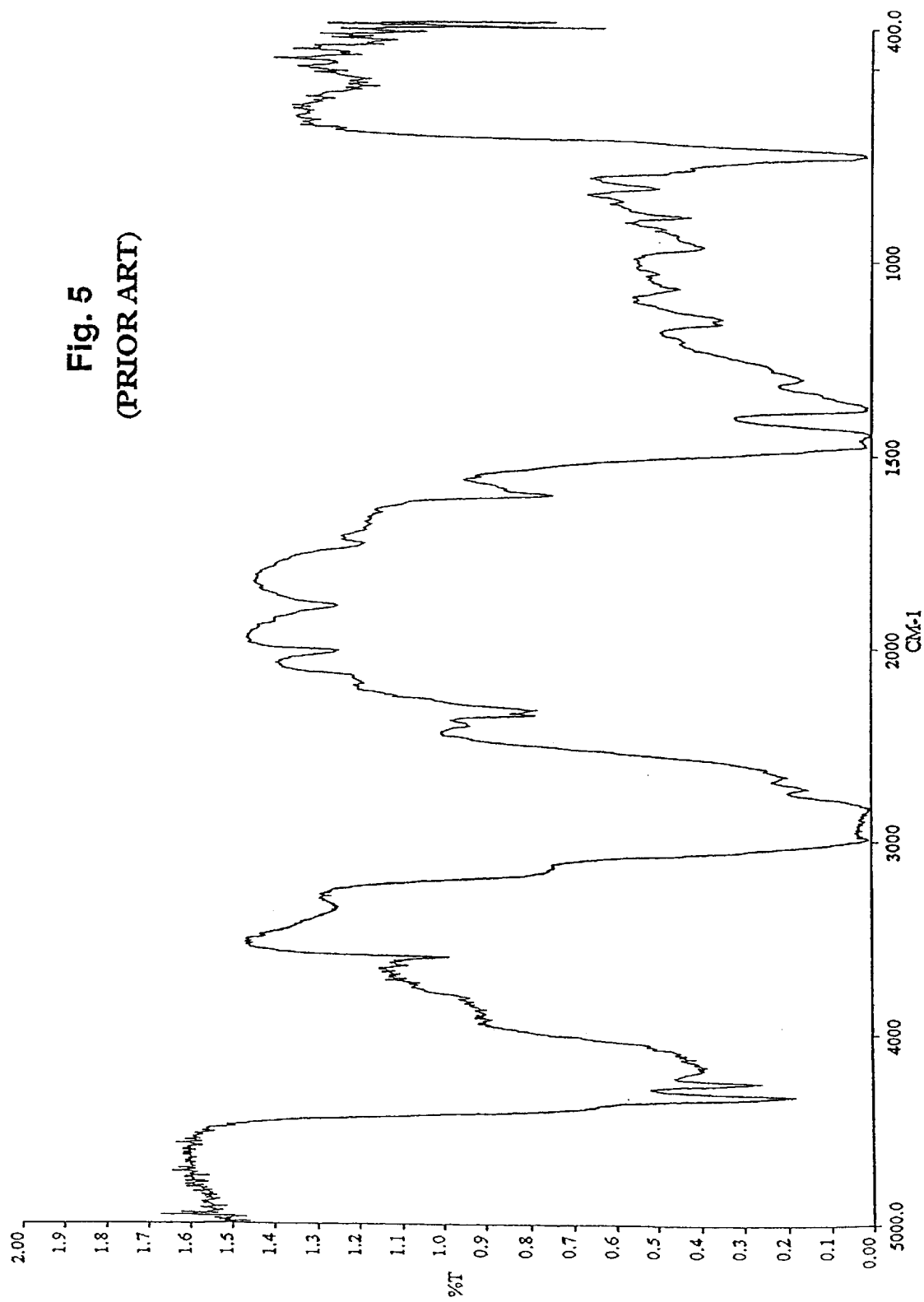
FIG. 5 shows the FTIR transmission spectrum of vaseline mounted on a Janos ECRAN Screen Cell.
Figure 6:
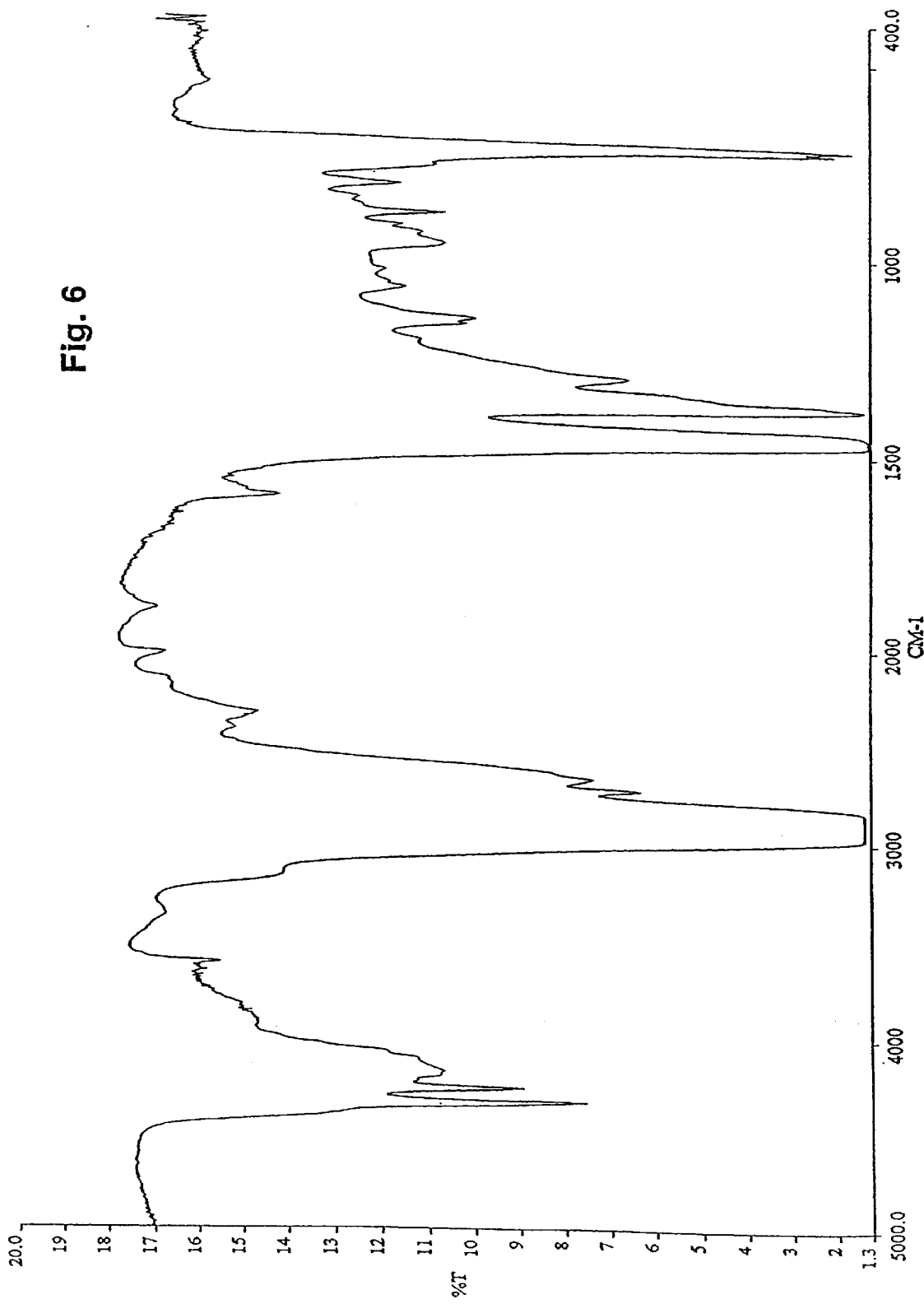
FIG. 6 shows the FTIR transmission spectrum of vaseline mounted on a pressed mesh according to the present invention.

FIGS. 5 and 6 show the spectrum of vaseline, as recorded when mounted on an ECRAN Screen Cell and a pressed mesh respectively. Here the difference in sensitivity is even more marked, with a ten-fold increase in sensitivity.

Figure 7:
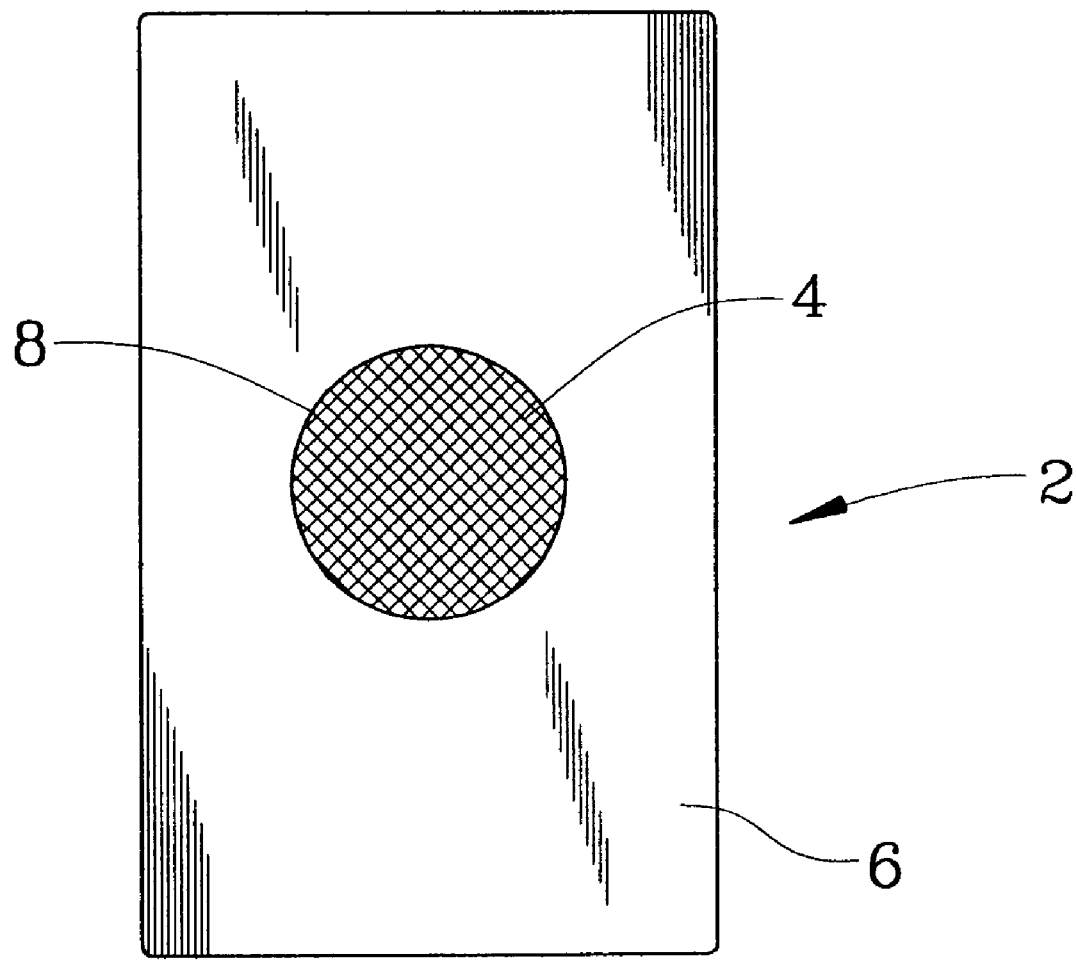
FIG. 7 shows a sample holder embodying the invention.

FIG. 7 illustrates a sample holder 2 embodying the invention. The sample holder 2 comprises a stainless steel mesh 4 supported in a card 6 having a central opening 8. The mesh is held between two layers of card laminated together. The mesh 4 is prepared from a mesh of 25 m diameter strands and about 80% transmission which has been pressed to a thickness of between 10 and 20 m and a transmission of about 60%.

The pressed mesh of the present invention has the advantages that it is cheap, easy to construct and use, chemically inert, and there is a complete absence of interfering absorptions. The formation of films is much closer to the optimum thickness of 10–20 microns than when coarse gauzes are used.

What is claimed is:

1. A spectroscopic sample holder comprising a mesh formed from strands of wire and supported in a frame having an open aperture, which mesh has been pressed to reduce its thickness to no more than 20 microns, the pressed mesh having a transmission of at least about 60%.

2. A sample holder as claimed in claim 1, wherein said wire is stainless steel.

3. A sample holder as claimed in claim 2, wherein the mesh has been thermally treated to improve the wettability in order to improve the uptake of liquid samples or solutions.

4. A sample holder as claimed in claim 2, wherein the mesh has been chemically treated to improve the wettability order to improve the uptake of liquid samples or solutions.

5. A sample holder as claimed in claim 1 wherein the thickness of the pressed mesh is in the range of 10–20 microns.

6. A sample holder as claimed in claim 1, wherein the mesh has been thermally treated to improve the wettability in order to improve the uptake of liquid samples or solutions.

7. A sample holder as claimed in claim 1, wherein the mesh has been chemically treated to improve the wettability order to improve the uptake of liquid samples or solutions.

8. A method of forming a spectroscopic sample holder comprising the steps of:

providing a mesh formed from wires, pressing said mesh between hardened dies so as to Seduce its thickness to no more than 20 microns and such that its transmission is at least about 60% and mounting said mesh in a holder having an open aperture.

9. A method as claimed in claim 8, wherein the pressure applied to the mesh is in the region of 150–250 MPa.

10. A method as claimed in claim 8 wherein said wire is stainless steel.

11. A method as claimed in claim 10, wherein after the mesh has been pressed the total thickness thereof is in the region of 10–20 microns.

12. A method as claimed in claim 8, wherein after the mesh has been pressed the total thickness thereof is in the region of 10–20 microns.

13. A method as claimed in claim 8, further comprising thermally treating the mesh to improve the wettability in order to improve the uptake of liquid samples or solutions.

14. A method as claimed in claim 8, further comprising chemically treating the mesh to improve the wettability in order to improve the uptake of liquid samples or solutions by washing the mesh in acid.

15. A method of forming a sample holder for spectroscopy, comprising:

providing a mesh formed from stainless steel wires of thickness in the region of 25 microns, said mesh having a transmission of about 80%, pressing said mesh between hardened dies so as to reduce its thickness to the region of 10–20 microns with a transmission of at least about 60%, and mounting said mesh in a holder having an open aperture.

* * * * *